United States Patent
Régnier et al.

(10) Patent No.: US 10,271,752 B2
(45) Date of Patent: *Apr. 30, 2019

(54) DETECTION/STIMULATION MICROLEAD IMPLANTABLE IN A VESSEL OF THE VENOUS, ARTERIAL OR LYMPHATIC NETWORK

(71) Applicant: SORIN CRM SAS, Clamart (FR)

(72) Inventors: Willy Régnier, Longjumeau (FR); Philippe d'Hiver, Chatillon (FR)

(73) Assignee: Sorin CRM SAS, Clamart (FR)

( * ) Notice: Subject to any disclaimer, the term of this patent is extended or adjusted under 35 U.S.C. 154(b) by 0 days.

This patent is subject to a terminal disclaimer.

(21) Appl. No.: 15/675,417

(22) Filed: Aug. 11, 2017

(65) Prior Publication Data

US 2017/0340224 A1   Nov. 30, 2017

Related U.S. Application Data

(63) Continuation of application No. 14/554,471, filed on Nov. 26, 2014, now Pat. No. 9,730,595.

(30) Foreign Application Priority Data

Nov. 27, 2013 (FR) .................................. 13 61708

(51) Int. Cl.
*A61N 1/05*   (2006.01)
*A61B 5/04*   (2006.01)
*A61B 5/00*   (2006.01)

(52) U.S. Cl.
CPC .............. *A61B 5/04* (2013.01); *A61B 5/6876* (2013.01); *A61N 1/05* (2013.01); *A61N 1/056* (2013.01); *A61N 1/057* (2013.01)

(58) Field of Classification Search
CPC ................ A61N 1/05; A61B 5/00; A61B 5/04
(Continued)

(56) References Cited

U.S. PATENT DOCUMENTS 8,868,213 B2    10/2014  Shan et al.
9,730,595 B2 *   8/2017  Regnier ................ A61N 1/056
(Continued)

FOREIGN PATENT DOCUMENTS

EP    0 993 840 A1    4/2000
EP    2 455 131 A1    5/2012
(Continued)

OTHER PUBLICATIONS

Foreign Search Report for French Patent Application No. FR 1361708, dated Mar. 28, 2014, 1 page.

*Primary Examiner* — Carl H Layno
*Assistant Examiner* — Jon Eric C Morales
(74) *Attorney, Agent, or Firm* — Foley & Lardner LLP

(57) ABSTRACT

A microlead has a distal active portion formed by a microcable including an electrically conductive core coated with an insulation layer, with a plurality of exposed areas forming the stimulation electrodes. The microcable has a three-dimensional preshape inscribed in a cylindrical envelope volume so as to match the target vessel wall. The microcable includes a plurality of exposed areas regularly distributed over the circumference of the cylindrical envelope volume considered in axial projection, the exposed zones extending only over an angular sector of the microcable considered in cross section, said angular sector facing the outside of the envelope volume of the preshape.

19 Claims, 1 Drawing Sheet

(58) Field of Classification Search
USPC .......................................................... 607/116
See application file for complete search history.

(56) References Cited

U.S. PATENT DOCUMENTS

| | | | | |
|---|---|---|---|---|
| 2006/0247751 | A1* | 11/2006 | Seifert | A61N 1/057 607/122 |
| 2009/0157136 | A1* | 6/2009 | Yang | A61B 5/0422 607/17 |
| 2012/0130464 | A1* | 5/2012 | Ollivier | A61N 1/056 607/122 |
| 2013/0096658 | A1 | 4/2013 | Shan et al. | |
| 2014/0135883 | A1* | 5/2014 | Regnier | A61N 1/05 607/116 |

FOREIGN PATENT DOCUMENTS

| | | |
|---|---|---|
| EP | 2 559 453 A1 | 2/2013 |
| EP | 2 581 107 A1 | 4/2013 |
| WO | WO-02/18006 | 3/2002 |

* cited by examiner

DETECTION/STIMULATION MICROLEAD IMPLANTABLE IN A VESSEL OF THE VENOUS, ARTERIAL OR LYMPHATIC NETWORK

CROSS-REFERENCE TO RELATED PATENT APPLICATIONS

This application is a continuation application of U.S. patent application Ser. No. 14/554,471, filed Nov. 26, 2014, is now U.S. Pat. No. 9,730,595, which is related to French Patent Application No. 1361708, filed Nov. 27, 2013, the priority of which is claimed and the disclosure of which is incorporated by reference in its entirety.

BACKGROUND

The invention relates to "active implantable medical devices" as defined by Directive 90/385/EEC of 20 Jun. 1990 of the Council of the European Communities. This definition includes implantable devices for continuous monitoring of the heart rhythm and to deliver if necessary electrical stimulation, defibrillation or resynchronization pulses to the heart. It also includes neurological devices, cochlear implants, medical drug pumps, implantable biological sensors, etc.

These devices include a housing generally designated as the generator electrically and mechanically connected to one or more intracorporeal leads provided with electrodes for contacting the tissue in which it is desired to apply stimulation pulses and/or to collect an electrical signal (myocardium, nerve, muscle, etc.).

The present invention more precisely relates to a detection/stimulation microlead intended to be implanted in the venous, arterial, or lymphatic networks. Performance of the stimulation of a heart chamber by an implantable lead in the coronary network will more specifically be described in the present application, but this application is not restrictive, and the microlead of the invention can be used in many other configurations and applications permitted by its very small diameter.

In this example of coronary leads for stimulating a left, atrial or ventricular, cavity of the heart, the lead is not inserted into the cavity to stimulate but in the coronary network, and is provided with an electrode for contacting the wall to the epicardium at the level of the left ventricle or of the left atrium, as appropriate. These leads thus stimulate the heart muscle via one or more point electrodes whose position is a function of the predefined trajectory of the cannulated vein.

With the lead not being placed within the cavity but against a wall, the importance of a correct orientation of the electric field generated by the electrode must be understood, so as to ensure the orientation of the electric field to the cardiac muscle through the vein wall, to reduce the pacing threshold and, consequently, the energy required for the stimulation.

With conventional leads, e.g. the Situs LV model sold by Sorin CRM, Clamart, France, and which is described in particular in EP 0993840 A1 (ELA Medical), the lead stimulates the cavity through an annular ring electrode blocked in the vein and contacting on the whole periphery thereof in the region of the stimulation site. The electric field is then distributed in all directions on 360°, which corresponds to an "annular" radiation. A part of the radiation will necessarily be oriented in the direction of the heart muscle due to the constant contact with the vein, which guarantees delivery of the stimulation energy of the cavity where the electrode has been implanted.

However, a significant portion of the electric field is not optimally used, as it is directed opposite to the heart muscle, which corresponds to an unnecessary energy for stimulation. Indeed, most of the electric field is distributed in the blood, whose electrical conductivity is higher than that of the muscle tissue, thus resulting in poor performance for electrical cardiac pacing.

WO 02/180006 A2 describes a lead of a similar type, wherein the distal end includes an included helical preshape, the diameter of which is between 2.5 and 20 mm, with regularly distributed electrodes at 120° on this preshape. The configuration of this preshape notably allows an effective and stable contact at the interface between the lead and the wall of great diameter vessels, the helical preshape mechanically pressing, by elasticity, the lead against the inner wall of the vessel.

A recent trend in the implantable stimulation lead in venous, arterial, or lymphatic network is the reduction in diameter, typically to a diameter of less than 2 French (0.66 mm), or reaching 0.5 French (0.17 mm). This is much lower than that of conventional leads such as the Situs LV model described above, the diameter of the active portion of which is of the order of 4 to 7 French (1.33 mm to 2.33 mm) or the leads such as those described in the WO 02/180006 A2 cited above.

The size of the lead body is indeed a factor directly related to the capabilities of controlled guiding of the lead, for example in the coronary venous network, which allows to select specific stimulation sites located in certain collateral veins. The very small diameter outside the active distal end of the lead thus allows cannulation of very thin veins of the coronary network, so far not used because of the excessive size of conventional coronary leads.

Such leads, which can be described as "microleads" are described for example in EP 2455131 A1, EP 2559453 A1 and EP 2581107 A1, all three on behalf of Sorin CRM SAS. The active portion of these microleads is constituted by a microcable having a diameter of about 0.5 to 2 French (0.17 to 0.66 mm) having a plurality of exposed portions forming a succession of individual electrodes constituting together a network of electrodes connected in series to multiply the points of stimulation in a deep area of the coronary network.

As described in particular in EP 2559453 A1 above, the very small diameter of the microcable can allow for introduction in a first vein ("go" vein), then by an anastomosis to a second vein ("return" vein) ascending therein. A very frequent presence of distal anastomosis in the coronary venous network has been found, that is to say that there is at the end of certain veins a passage to another vein, therefore with a possibility of communication between two separate veins at the anastomosis, via their respective distal ends. This makes it possible, with a single lead, to simultaneously stimulate two relatively remote areas, because they are located in two separate veins. The double effect of the distance of these two areas and of the multiplication of points of stimulation in each area provides a particularly beneficial effect on the resynchronization of the functioning of the heart.

Another advantage of the small diameter of the active part of the lead is that it avoids the blockage of a part of the blood flow in the vein, which would result in a deficiency of the venous network irrigation downstream of the lead tip.

Reducing the diameter of the lead is nevertheless not devoid of drawbacks. Indeed, when the diameter of the lead is substantially lower than that of the vein, it is difficult to assure the permanent contact of the electrodes. The exposed portion of the microcable which forms an electrode may thus be in an intermediate, "floating", position in the middle of the vein, the contact points between the microcable and the vein wall occurring on electrically isolated areas.

This is particularly true in the case of microcables passing through an anastomosis. Indeed, if the veins are of small diameter, typically less than 1 French (0.33 mm) in the region of the anastomosis, beyond the anastomosis they may join the coronary sinus after passing the left ventricle, and in this case their diameter increases. The very thin microcable which has allowed passing the anastomosis may then move into a region of relatively large diameter, thereby with a difficulty in establishing a stable contact between the electrodes and the vein wall in the area.

This drawback (no guaranteed contact) is the counterpart to the advantage mentioned above to avoid the obstruction of blood flow in the vein. In contrast, the larger diameter leads including an annular stimulation ring blocked over the entire periphery of the vessel ensure contact with the target tissue, but necessarily involve an obliteration of this vessel which can have deleterious effects. Furthermore, from the electrical point of view, it is important to ensure, firstly, the effectiveness of the stimulation despite a vessel having a diameter larger than that of the stimulation microcable and, secondly, optimized power consumption even with a configuration of only three electrodes oriented at 120° applicable in anastomoses.

SUMMARY

Exemplary embodiments disclosed herein provide a microlead structure that provides an effective stimulation despite a microcable diameter well below the size of the vessel, and which:
- improves contact between the vessel tissue and the microlead stimulation electrodes;
- directs the electric field in the direction of the target tissue to be stimulated (heart muscle) in order to optimize the electrical performance by not unnecessarily dissipating a significant portion of the stimulation energy; and
- provides distribution of the electrodes along the microlead in well localized stimulation regions, maximizing the overall impedance of the lead so as to reduce the stimulation threshold and therefore the energy consumption.

Moreover, the exemplary embodiments may further provide the following characteristics, from the mechanical point of view:
- the microcable stimulating area has a typical outer diameter of about 1.5 French (0.5 mm) to ensure the passage in anastomoses, and in the microcatheter used during implantation, with an "isodiametric" profile; that is to say an even diameter throughout the length of the active part of the microlead;
- the distal active part is flexible enough not to hurt the vein, and must maintain continuous contact with the inner vessel wall to reduce the risk of displacement or loss of stimulation; and
- the contact force between the electrode and the inner wall of the vessel should be as small as possible, ideally a simple flush contact to reduce the risk of inflammation and thrombosis between the vessel and the microcable at the contact point.

The invention discloses embodiments of a detection/stimulation microlead having a distal active portion constituted by a microcable of a diameter at most equal to 2 French (0 66 mm) including an electrically conductive core coated with an insulation layer. This microcable includes at least one stimulation zone wherein the insulation layer has a plurality of exposed zones forming respective stimulation electrodes, and has in the stimulation area a three-dimensional preshape configured such that the microcable matches with the target vessel wall in the stimulation area. The three-dimensional preshape can occur in a cylindrical envelope volume whose diameter is chosen to be, in the free state of the microcable, greater than the diameter of the target vessel.

In certain preferred embodiments of the invention, the microcable includes, in the region of the three-dimensional preshape, at least three of the exposed areas—these areas being disposed at respective locations of the microcable located on the cylindrical envelope volume, and further, uniformly distributed on the circumference of the cylindrical envelope volume seen in axial projection. Furthermore, the surface without insulating coating of each exposed area may be between 0.1 mm$^2$ and 1 mm$^2$. In some embodiments, the surface may be less than 0.3 mm$^2$.

This configuration, according to the invention, provides the following benefits from the electrical point of view:
- The surfaces of the electrodes being reduced, the impedance Z increases and the power decreases for a given stimulation voltage V (optimization of the $V^2/Z$ parameter);
- The uniform distribution of the three electrodes on 360° ensures at least one of them is best oriented towards the excitable tissue, thus reducing the distance to the tissue which also reduces the power required to stimulate;
- This best oriented electrode is in contact with the vein wall with minimal contact pressure, which minimizes inflammation and therefore reduces the progressive increase in the stimulation threshold, with a favorable long-term effect on consumption; and
- The number of three electrodes per zone as well as their remoteness limit the efficiency losses associated with the reducing of the current emitted because of their mutual influences.

According to various advantageous subsidiary characteristics:
- The surface without insulating coating of each exposed area may be 0.1 mm$^2$-1 mm$^2$;
- The microcable may include three exposed areas disposed at respective locations distributed at 120° on the circumference of the cylindrical envelope volume considered in axial projection;
- The exposed zones may extend only over an angular sector of the microcable considered in cross section, and the angular sector may be outward of the envelope volume of the preshape;
- The surface devoid of the insulating coating of each exposed area may be less than 0.3 mm$^2$, and in other embodiments, less than 0.1 mm$^2$;
- The three-dimensional preshape may be a helical preshape;
- The at least three exposed areas may be disposed at respective locations of the microcable regularly distributed in the longitudinal direction on the cylindrical envelope volume; and/or
- The microlead may include two distinct stimulation areas separated by an elongation and retention spacer area, shaped to make the microlead elastically deformable in the longitudinal direction under the effect of axial tensile/compression exerted on the microlead in the proximal region over the elongation area.

In one exemplary embodiment, a detection/stimulation microlead for implantation in a target vessel of the venous, arterial, or lymphatic network for stimulation of tissue in the region of the target vessel is provided. The microlead includes a distal active portion including a microcable of a diameter at most equal to 2 French (0.66 mm) and having an electrically conductive core coated with an insulation layer. The microcable further includes at least one stimulation area having a plurality of exposed areas formed in the insulation layer forming a plurality of stimulation electrodes, wherein the surface without insulating coating of each exposed area is between 0.1 mm$^2$ and 1 mm$^2$. In preferred embodiments, the surface is less than 0.3 mm$^2$, and in other preferred embodiments, less than or equal to 0.1 mm$^2$. The microcable further includes a three-dimensional preshape at the stimulation area configured so that the microcable contacts the wall of the target vessel in the stimulation area. The three-dimensional preshape is enclosed in a cylindrical envelope volume whose diameter is selected to be in the free state of the microcable, greater than the diameter of the target vessel. The plurality of exposed areas are disposed at respective locations of said microcable on said cylindrical envelope volume, these locations being uniformly distributed on the circumference of the cylindrical envelope volume considered in axial projection.

In another exemplary embodiment, a method of stimulating distinct areas of tissue through the venous coronary network through an anastomosis is provided. The method includes introducing a microlead into the venous coronary network through the coronary sinus and advancing the lead so as to position a first set of stimulation electrodes of the microlead in a first vessel, a second set of stimulation electrodes in a second vessel, and an intermediate region through an anastomosis providing passage from the first vessel to the second vessel. The microlead comprises an electrically conductive core coated with an insulation layer and a diameter no greater than 2 French (0.66 mm). The first set and the second set of stimulation electrodes are formed by exposed areas formed in the insulation layer and are separated by the intermediate region. Each of the first set and the second set of stimulation electrodes forms a stimulation area, and wherein the stimulation area comprises a three-dimensional preshape configured so that the microlead contacts the wall of the target vessel in the stimulation area. The three-dimensional preshape is comprised in a cylindrical envelope volume with a diameter in the free state of the microcable, greater than the diameter of the target vessel. The stimulation electrodes in each stimulation area are disposed at respective locations of said microlead on said cylindrical envelope volume, these locations being uniformly distributed on the circumference of the cylindrical envelope volume in axial projection. The method further includes providing stimulation through the target vessels by the first and second set of electrodes.

DRAWINGS

Further features, characteristics and advantages of the present invention will become apparent to a person of ordinary skill in the art from the following detailed description of preferred embodiments of the present invention, made with reference to the drawings annexed, in which like reference characters refer to like elements and in which:

FIG. 1 generally illustrates the myocardium, with the main veins of the coronary network in which a lead according to the invention has been introduced for the stimulation of the left ventricle.

DETAILED DESCRIPTION

An exemplary embodiment of the microlead of the invention, applied to the stimulation of a heart chamber by a lead implanted in the coronary network, will now be described. As indicated above, this application is not restrictive, and the microlead of the invention can be used in many other applications in view of its ability to be implanted in the deep venous, arterial or lymphatic networks.

Figure 1:
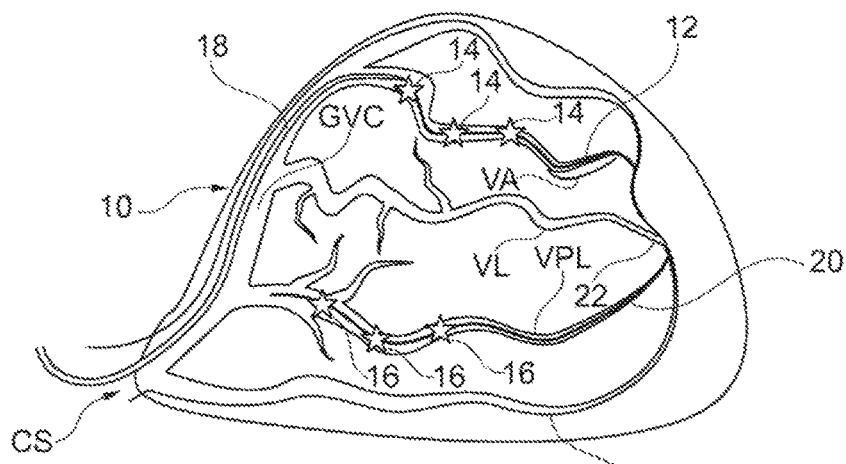

FIG. 1 generally illustrates the myocardium and the main coronary vessels of the coronary network, wherein a lead according to the invention is introduced to stimulate the left ventricle. This lead is endocardially implanted in the venous coronary network via the superior vena cava, the right atrium and the input of the venous coronary sinus CS. The venous coronary network then develops into several branches from the great cardiac vein GVC, these branches including the posterolateral vein VPL, the lateral vein VL, the anterolateral vein VA and the posterior vein VP.

Figure 2:
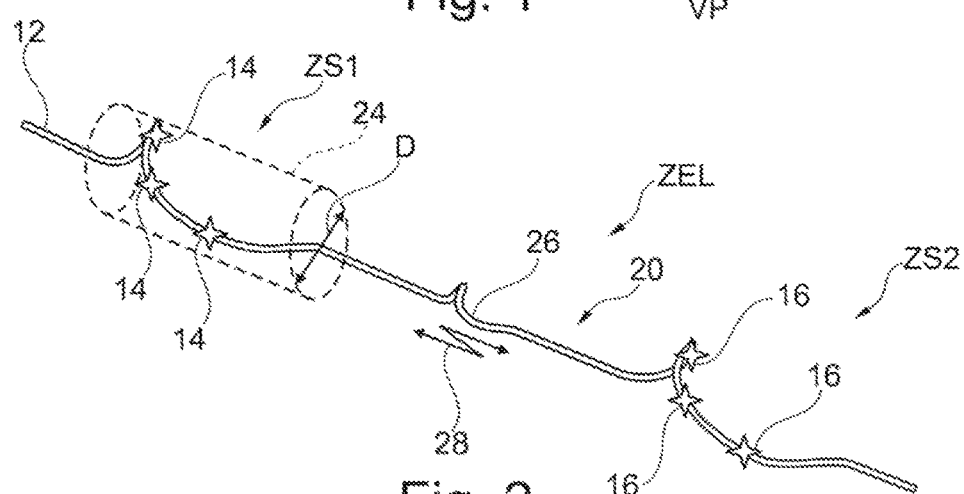
FIG. 2 illustrates the end portion of the microcable according to the invention for the multi-zone stimulation.

Reference 10 generally refers to the lead according to the invention, which includes in its active part a microcable 12 whose distal part is shown in FIG. 2 in isolation. The lead 10 further includes, in its proximal region, a microcatheter 18 entering the coronary sinus and the great cardiac vein GVC to the opening of the anterolateral vein VA.

The microcable 12 is introduced into the anterolateral vein VA and carries a plurality of stimulation electrodes 14 to stimulate the left ventricle from multiple sites in this vein VA. The microcable 12 also carries, at a distance from the electrodes 14, another set of electrodes 16 to stimulate the left ventricle from a different vein, e.g. via a posterolateral vein VPL via a communication by an anastomosis 22 connecting the anterolateral vein VA and the posterolateral vein VPL. The microcable crosses this anastomosis 22 and the more distal regions of both VA and VPL veins along an intermediate portion 20 free of the electrodes.

With this configuration, it is possible not only to stimulate the left ventricle at several points of one of the veins (because of the multiplication of the electrodes 14 or 16), but also to provide two relatively remote stimulation areas, respectively the area of the electrodes 14 and the area of the electrodes 16, located in two different proximal regions of the two veins in which it would be difficult to stabilize or fix conventional left ventricular pacing leads because of the large diameter of the mouth of these veins.

FIG. 2 describes the distal active portion of the microcable 12, with the first set of electrodes 14 and the second set of electrodes 16, the two sets being separated by the intermediate portion 20.

The microcable 12 includes an electrically conductive core provided with an insulating coating on its entire length, except for occasionally exposed areas constituting the detection/stimulation electrodes 14 and 16. In regards to the structure of the microcable 12, the core thereof is preferably a multi-stranded structure in which each strand is preferably made of nitinol (NiTi alloy) or MP35N-LT (35% Ni, 35% Co, 20% Cr and 10% Mo), materials whose main advantage is their extreme fatigue endurance, with a sheath coating of platinum-iridium or tantalum (for radiopacity and biostability). Such a structure allows optimizing the response to the requirements of corrosion resistance at the electrodes, and of endurance against cardiac movements. These microcables are available for example from the company Fort Wayne Metals Inc., Fort Wayne, USA.

The core wire is coated with a thin insulation layer, on the order of 25 microns thick, for example by coextrusion of the conductor or by a heat shrinkable tube. The insulator may be a thin layer of parylene (e.g., type C). In this case, windows of varying complexity are created along the microcable, e.g. by plasma ablation, to form the electrodes 30. To improve electrical performance, these areas can further be coated, for example with titanium nitride. In other embodiments, the insulator may be a polyurethane tube interrupted at the locations of electrodes 14 and 16. In other embodiments, the insulator may be one or more layers consisting of tubes made of PET (polyethylene terephthalate), fluoropolymer, PMMA (polymethyl methacrylate), PEEK (polyetheretherketone), polyimide or other suitable similar material.

A particular advantage of this structure results from the very flexible and floating (floppy) characteristics of the microcable, which provides excellent atraumaticity. Such a microcable does not attack the tissue and thus preserves the cells adjacent to the electrodes.

In the configuration described herein, the microcable includes a single conductor, so that the exposed regions form electrodes, which, from the electrical point of view, are connected together and are at the same potential. This monopolar configuration is however not limiting, and the invention is equally applicable to a multipolar lead, with a microcable including a plurality of separate conductors electrically insulated from each other, for example as a bundle of insulated conductors stranded together, each being provided with one or more exposed areas forming respective electrodes.

The microcable has a three-dimensional preshape at the location of the electrodes 14 which form a first stimulation zone ZS1, and at the location of the electrodes 16 which form a second stimulation zone ZS2. This preshape is designed to promote the electrode contact with the vessel wall, and thus the electrical performance.

The two stimulation areas ZS1 and ZS2 preferably have an identical configuration. The three-dimensional preshape of the microcable 12 to the location of each stimulation area is inscribed in a cylindrical envelope volume 24 whose diameter D is chosen to be, in the free state of the microcable, greater than the diameter of the target vessel. In some embodiments, the diameter D of the cylindrical envelope volume may be at least twice the diameter of the target vessel. For example, the stimulation area may have a diameter of 12 mm for a microlead to be implanted into a target vein of 2 to 6 mm in diameter.

Preferably, the three-dimensional preshape is a helical one in the cylindrical envelope 24. Thus, when the lead is inserted into the vein, the helical shape of the microcable is naturally press against the walls, ensuring a permanent contact. Furthermore, the three exposed areas 14 or 16 are, in the longitudinal direction, arranged at respective locations evenly distributed over the volume of the cylindrical envelope 12 of the microcable.

To ensure the stability of the assembly, a preshape 26 is added to the intermediate portion 20 free of the electrode, so as to constitute an elongation area ZEL to facilitate elongation of the lead in the axial direction (arrows 28), especially during the stresses exerted on the microcable with each heartbeat, or if the patient moves and performs further movement (lifting of the arm, etc.). These efforts will be absorbed by deformation of the elongation area ZEL without moving the stimulation areas ZS1 and ZS2, so with no effect on the positioning of the electrodes. The preshape 26 of the elongation area ZEL is selected so that its diameter is smaller than the diameter of the target vein, and its shape is selected so as to have a greater flexibility in axial direction than of the preshapes of the stimulation zones ZS1 and ZS2. This elongation area also provides a complementary retention function of the microlead into the vein.

Figure 3:
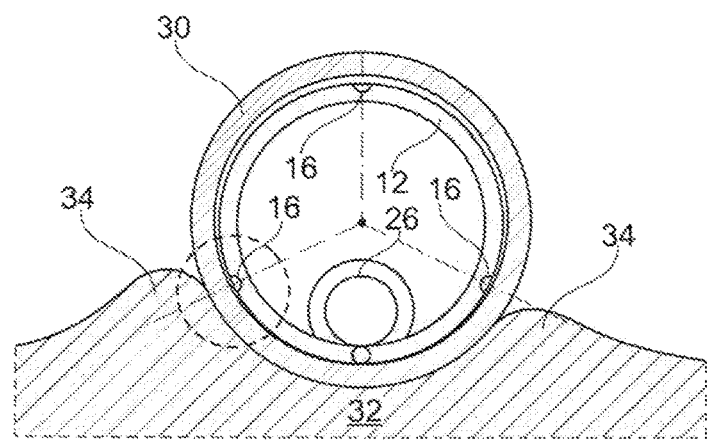
FIG. 3 is an end view, in an axial direction, of the microlead of the invention introduced into a vessel of the coronary network, showing the method by which the contact is provided at the stimulation site, by which the electrical field can be specifically distributed in direction of the heart muscle.

FIG. 3 is an end view, in an axial direction (shown in section), of an embodiment of the microlead in the stimulation area ZS2, this microlead being inserted into a vessel of the coronary system. In this view, it can be seen that there are three electrodes 16 in the stimulation area ZS2 (it is the same for the electrodes 14 of the stimulation area ZS1) distributed at 120°, in axial view, on the surface of the envelope volume 24. This configuration ensures contact at all times of at least one of the electrodes (the electrode located at the bottom left in the example of FIG. 3) with the inner vessel wall 30, regardless of the angular configuration of the preshape carrying the electrodes with respect to the vein 30.

Indeed, from the anatomical point of view, the interface between the cardiac muscle 32 and the coronary vein 30 does not appear as a flat surface, but with a lateral flange 34 (fatty deposits) ensuring that the extent of contact between the vein 30 and the cardiac muscle 32 anatomically occurs on an angular sector. This increases the chances of contact of at least one of the electrodes 16 with the inner wall of the vein 30 in the region of this angular sector, thereby allowing a direct transmission of electrical energy from the electrode 16 to the heart muscle 32.

The number and distribution of electrodes 16 (three electrodes, placed at 120°) are considered preferred but are not a limitative configuration. There could be a higher number of electrodes, for example four in number, leading to a superior warranty of contact with the wall of the vein, but at the cost of higher electrical losses. In this case, if only one electrode is in contact with the heart tissue, three-quarters of the energy will be dissipated in the blood and not to the heart muscle against only two thirds in the case of a three electrode configuration.

Furthermore, the exposed areas constituting the electrodes 14 or 16 extend only over an angular sector of the microcable considered in cross section. These are "segment" electrodes rotated outwardly of the envelope volume of the preshape 24, so in the direction of the inner vessel wall 30, in the area wherein the possibility of contact with the wall is maximum.

The exposed surface of each electrode 14 or 16 is typically constituted by a hole formed in the insulating material of the sheath to a diameter of 0.2 mm, for example by firing a low-power laser to locally melt the insulation of the microcable without damaging the core conductor thereof. The total area of all the electrodes 14 of the stimulation area ZS1 (or of all electrodes 16 of the stimulation area ZS2) is between 0.3 mm$^2$ and 3 mm$^2$ (with certain embodiments having three electrodes each with an area of between 0.1 mm$^2$ and 1 mm$^2$), a value from several times lower than conventional leads such as the Situs LV model initially described, the surface of the annular electrode is about 6 mm$^2$.

It is thus possible to stimulate the heart muscle by concentrating the electric field on a small area corresponding to the small exposed surface area, resulting in a significant increase in the impedance of the lead leading to a much lower energy delivered by the generator at each stimulation pulse, for the same or even greater efficacy.

What is claimed is:

1. A detection/stimulation microlead for implantation in a target vessel for stimulation of tissue in a region of the target vessel, the microlead comprising:
   an electrically conductive core coated with an insulation layer;
   a plurality of exposed areas formed in the insulation layer and comprising a plurality of stimulation electrodes; and
   a three-dimensional preshape formed at one or more of the plurality of exposed areas, the three-dimensional preshape structured such that the exposed area of the microlead contacts a wall of the target vessel,
   wherein the three-dimensional preshape is structured so that portions having a largest diameter contact the vessel wall, the largest diameter being greater than a diameter of the target vessel; and
   wherein the plurality of electrodes are disposed at respective locations of said microlead on said three-dimensional preshape, these locations being uniformly distributed on a circumference of the three-dimensional preshape considered in an axial projection; and
   wherein the plurality of electrodes are included within two distinct stimulation areas separated by an intermediate region.

2. The microlead of claim 1, wherein the plurality of electrodes are uniformly distributed on a circumference of the three-dimensional preshape considered in an axial projection.

3. The microlead of claim 1, wherein the largest diameter is at most equal to 2 French (0.66 mm).

4. The microlead of claim 1, wherein the plurality of electrodes have an area between 0.1 mm$^2$ and 1 mm$^2$.

5. The microlead of claim 1, wherein the three-dimensional preshape is a helical preshape.

6. The microlead of claim 1, wherein the plurality of electrodes are disposed at respective locations of the microlead regularly distributed in a longitudinal direction on a cylindrical envelope volume.

7. The microlead of claim 1, wherein the intermediate region comprises a retention and elongation area, elastically deformable in a longitudinal direction under an effect of tensile/compression axial stress exerted on the microlead in a proximal area with respect to the elongation area.

8. The microlead of claim 7, wherein the intermediate region comprises a preshape formed in the microlead in a free state.

9. The microlead of claim 8, wherein the preshape of the intermediate region is selected to have a diameter smaller than the diameter of the target vessel.

10. The microlead of claim 1, wherein three-dimensional preshape has a diameter of at least twice the diameter of the target vessel.

11. A method of stimulating distinct areas of tissue via a venous coronary network, comprising:
    introducing a microlead into the venous coronary network through a coronary sinus;
    advancing the microlead so as to position a first set of stimulation electrodes of the microlead in a first vessel, a second set of stimulation electrodes in a second vessel, and an intermediate region through an anastomosis providing passage from the first vessel to the second vessel, wherein the microlead comprises a three-dimensional preshape structured so that the first set of electrodes and the second set of electrodes contact a wall of a target vessel and so that portions having a largest diameter contact the vessel wall, the largest diameter being greater than a diameter of the target vessel; and
    providing stimulation through the target vessels by the first and second set of electrodes.

12. The method of claim 11, wherein the plurality of electrodes are disposed at respective locations of said microlead on said three-dimensional preshape, these locations being uniformly distributed on a circumference of the three-dimensional preshape considered in an axial projection.

13. The method of claim 11, wherein the first set and the second set of stimulation electrodes are separated by the intermediate region and the intermediate region is elastically deformable in a longitudinal direction under an effect of tensile/compression axial stress exerted on the microlead in its proximal area with respect to the elongation area.

14. The method of claim 12, wherein the intermediate region of the microlead comprises a preshape formed in the microlead in a free state, wherein the preshape of the intermediate region of the microlead is selected to have a diameter smaller than the diameter of the target vessel.

15. The method of claim 11, wherein the first set and the second set of stimulation electrodes each have an area between 0.1 mm$^2$ and 1 mm$^2$.

16. A detection/stimulation microlead for implantation in a target vessel for stimulation of tissue in a region of the target vessel, the microlead comprising:
    a three-dimensional helical preshape at a stimulation area, the stimulation area comprising a plurality of electrodes, and the three-dimensional helical preshape configured such that the microlead contacts a wall of the target vessel in the stimulation area;
    wherein the three-dimensional helical preshape is structured so that portions having a largest diameter contact the vessel wall, the largest diameter being greater than a diameter of the target vessel; and
    wherein the plurality of electrodes are disposed at respective locations of said microlead on said three-dimensional helical preshape.

17. The microlead of claim 16, wherein the three-dimensional preshape has a diameter of at least twice the diameter of the target vessel.

18. The microlead of claim 16, wherein the largest diameter is at most equal to 2 French (0.66 mm).

19. The microlead of claim 16, wherein the plurality of electrodes have an area between 0.1 mm$^2$ and 1 mm$^2$.

* * * * *